United States Patent [19]

Sembaev et al.

[11] Patent Number: 5,698,701

[45] Date of Patent: Dec. 16, 1997

[54] CATALYTIC COMPOSITION FOR THE OXIDATIVE AMMONOLYSIS OF ALKYLPYRIDINES

[75] Inventors: Dauren C. Sembaev; Faina A. Ivanovskaya, both of Almaty, Kazakhstan; Ernest M. Guseinov, Moscow, Russian Federation; Roderick J. Chuck, Brig-Glis, Switzerland

[73] Assignees: Lonza Ltd., Gampal/Valais, Switzerland; Institute of Chemical Science of the National Academy of Science of the Republic of Kazakstan, Almaty, Kazakhstan

[21] Appl. No.: 732,343

[22] PCT Filed: May 22, 1995

[86] PCT No.: PCT/EP95/01945

§ 371 Date: Jan. 7, 1997

§ 102(e) Date: Jan. 7, 1997

[87] PCT Pub. No.: WO95/32055

PCT Pub. Date: Nov. 30, 1995

[30] Foreign Application Priority Data

May 23, 1994 [KZ] Kazakhstan ............... 940561.1
Aug. 11, 1994 [WO] WIPO ............... PCT/EP94/02676

[51] Int. Cl.$^6$ .................................................. C07D 213/84
[52] U.S. Cl. ............................................................. 546/286
[58] Field of Search .................. 546/286, 287; 502/308, 309, 312

[56] References Cited

U.S. PATENT DOCUMENTS

| 3,799,888 | 3/1974 | Suvorov et al. | 252/469 |
|---|---|---|---|
| 3,959,297 | 5/1976 | Ishioka et al. | 260/294.9 |
| 3,970,657 | 7/1976 | Elion et al. | 260/294.9 |
| 4,939,260 | 7/1990 | Inoue et al. | 546/286 |
| 4,963,687 | 10/1990 | Saito et al. | 546/286 |
| 5,032,253 | 7/1991 | Wang et al. | 208/254 |
| 5,130,285 | 7/1992 | Wang et al. | 502/309 |
| 5,227,356 | 7/1993 | Hess et al. | 502/217 |

FOREIGN PATENT DOCUMENTS

| 0339680 | 11/1989 | European Pat. Off. . |
|---|---|---|
| 0514682 | 11/1992 | European Pat. Off. . |
| 0290996 | 10/1995 | European Pat. Off. . |
| 2264023 | 2/1975 | France . |
| 595350 | 3/1975 | Switzerland . |
| 1317064 | 5/1973 | United Kingdom . |

*Primary Examiner*—C. Warren Ivy
*Assistant Examiner*—Charanjit S. Aulakh
*Attorney, Agent, or Firm*—Fisher, Christen & Sabol

[57] ABSTRACT

A new catalytic composition, comprising the oxides of vanadium, titanium, zirconium and molybdenum is disclosed. The new catalytic composition is applied in the oxidative ammonolysis of alkylpyridines.

14 Claims, No Drawings

CATALYTIC COMPOSITION FOR THE OXIDATIVE AMMONOLYSIS OF ALKYLPYRIDINES

This application is a 371 of PCT/EP95/01945 which is now published as WO95/32055 on Nov. 30, 1995.

BACKGROUND OF THE INVENTION

1. Field of the Invention

This invention relates to catalytic compositions, their use in the oxidative ammonolysis of alkylpyridines and to a process for the production of cyanopyridines.

Preferably the catalytic compositions are used for the oxidative ammonolysis of 3-methylpyridine and 2-methyl-5-ethylpyridine to the corresponding 3-cyanopyridine.

3-Cyanopyridine is an intermediate for nicotinic acid or nicotinic acid amide which are essential vitamins of the B-complex.

2. Background Art

The oxidative ammonolysis of alkylpyridines is well known in the art. A great variety of catalyst systems have been disclosed but so far no process is known which can adequately satisfy the needs of a commercial process on a technical scale.

Reference is made to the USSR inventors certificate No. 891 142, wherein a catalyst for the ammonolysis of alkylpyridines consisting of the oxides of vanadium, tin and titanium is described. The maximum yield achieved for the conversion of for (e.g.) instance 2-methyl-5-ethylpyridine is 63%. The main drawback of this catalytic composition therefore is its low activity and selectivity.

From Swiss patent 595 350, it is further known that 2-methyl-5-ethyl pyridine can be converted to 3-cyanopyridine over a supported mixed oxide catalyst composed of oxides of vanadium, zirconium or titanium and optionally of tungsten. The yields obtained with this catalyst range between 60% and 75%. This catalyst is also not satisfactory due to its low selectivity and activity. A further drawback is the rather complicated procedure for producing this supported catalyst.

BROAD DESCRIPTION OF THE INVENTION

The object of the present invention is to provide catalytic compositions with further improved catalytic activity and performance and therefore to provide an improved process for oxidative ammonolysis of alkylpyridines especially with respect to selectivity and yield.

The catalytic composition of the present invention according to claim 1 comprises the oxides of vanadium, zirconium, titanium and molybdenum having a molar ratio of $V_2O_5$ to $TiO_2$ to $ZrO_2$ from 1:1:2 to 1:12:25 and a $MoO_3$ content of 0.54 to 2.6 weight percent relating to $V_2O_5$.

A preferred catalytic composition has a molar ratio of $V_2O_5$ to $TiO_2$ to $ZrO_2$ from 1:3:4 to 1:8:16 and a $MoO_3$ content of 0.54 to 1.15 weight percent relating to $V_2O_5$. In order to prepare the catalytic composition one can use the respective oxides itself but it is also possible to use precursor compounds which are later converted into the oxides. Such precursor compounds are for example: vanadiumoxide, the ammoniummetavanadate; zirconiumoxide, the zirconylchloride; titaniumoxide, the metatitaniumacid; and for the molybdenumoxide, the ammoniummolybdate.

The preparation of the catalytic composition can as a rule be accomplished by mixing the compounds in a suitable milling device, granulating or tabletting the mixture and finally drying the granules or tablets at a temperature of about 100° C. to 120° C. in a stream of air. The catalyst undergoes wiht advantage a subsequent thermal treatment at temperatures up to 650° C.

The ready prepared catalyst can then be charged into the reactor, wherein after an activation phase under reaction conditions, it is able to demonstrate its properties with respect both to high activity and selectivity at high loadings of the alkylpyridine and also with respect to long service life.

The catalytic composition of the present invention is especially suitable for the oxidative ammonolysis of alkylpyridines in presence of ammonia, an oxygen containing gas and if necessary water vapour. Preferred application of the catalytic composition is the conversion of 3-methylpyridine or 2-methyl-5-ethylpyridine to 3-cyanopyridine. The following process conditions have been proved to be suitable.

Air is generally used as the oxygen-containing gas. Thus air offers the advantage that oxygen is already diluted with inert components. The partial pressure of oxygen can be advantageously regulated by further dilution with a suitable inert gas, for example nitrogen, or by recycling part or most of the oxygen-lean exhaust gases.

Two advantages over the processes from the known state of the art is offered in the conversion of 3-methylpyridine, which according to the invention not only needs no addition of water vapour, but also uses a practically stoichiometric quantity or a small molar excess of ammonia.

The gaseous feed of the reactants in the case of the oxidative ammonolysis of 3-methylpyridine is accordingly composed of a molar ratio of3-methylpyridine to ammonia to air (calculated on the basis of oxygen) from 1:1:1.5 to 1:8.5:60.

A preferred gaseous feed is composed of a molar ratio of 3-methylpyridine to ammonia to air (calculated on the basis of oxygen) from 1:1:2 to 1:4:60

The gaseous feed of the reactants in the case of the oxidative ammonolysis of 2-methyl-5-ethylpyridine is composed of a molar ratio of 2-methyl-5-ethylpyridine to ammonia to air (calculated to $O_2$) and to water vapour from 1:20:20:60 to 1:60:70:330. The temperature in the reaction zone of the catalyst bed ranges expediently between 280° C. and 400° C. and preferably between 310° C. and 380° C.

The characteristics of the catalytic composition also with respect to life-time allow the process to be run continuously on a large scale-basis.

The maximum yield achieved with 3-cyanopyridine upon feeding up to 150 g per liter per hour of catalyst of 3-methylpyridine reaches 99%, and with 2-methyl-5-ethylpyridine up to 120 g per liter per hour of catalyst reaches 85%.

EXAMPLES

Example 1

36.4 g of vanadiumpentoxide, 48.0 g of titaniumdioxide, 197.2 g of zirconiumdioxide and 0.42 g of molybdenumtrioxide in the molar ratio $V_2O_5:TiO_2:ZrO_2$=1:3:8 and 1.15 wt. % $MoO_3$ based on vanadiumpentoxide, were ground and mixed in a bail mill. The mixture was moulded into granules of 5×5 mm and thermally treated at a temperature of 100°–120° C. for 6 hours in a flow of air. The obtained catalyst in the quantity of 60 cm$^3$ (82 g) was loaded into a tube reactor made of stainless steel (internal diameter 20 mm, length 1000 mm). A mixture of the reagents, consisting of 2-methyl-5-ethylpyridine, air, ammonia, water vapour was passed through the catalyst layer at a temperature of 340° C. The feeding rate (gram per 1 liter catalyst per 1 hour=gl$^{-1}$h$^{-1}$) was: 2-methyl-5-ethylpyridine—72 gl$^{-1}$h$^{-1}$, air—1500 liters, ammonia—228 $gl^{-1}h^{-1}$ and water—583.3 $gl^{-1}h^{-1}$ corresponding to a molar ratio of 2-methyl-5-ethylpyridine to oxygen to ammonia to water of 1:47:45:108. Accordingly 21.6 g of 2-methyl-5-ethylpyridine was fed over 10 hours. The conversion was complete. 15.0 g of 3-cyanopyridine was obtained corresponding to a yield of 80.5% from theory. The output of 3-cyanopyridine was 49.8 $gl^{-1}h^{-1}$.

Example 2

A catalyst as described in example 1 was used. A mixture consisting of 3-methylpyridine, air and ammonia was passed through the catalyst at a temperature of 330° C. The feeding rate (gram per 1 liter catalyst per 1 hour=$gl^{-1}h^{-1}$) was: 3-methylpyridine—84 $gl^{-1}h^{-1}$, air–2000 liters, ammonia—9.92 $gl^{-1}h^{-1}$ corresponding to a molar ratio of 3-methylpyridine:$O_2$:$NH_3$=1:40:1.3. Accordingly 25.5 g of 3-methylpyridine was fed over 10 hours. The conversion was complete. 26.8 g of 3-cyanopyridine was obtained corresponding to a yield of 95.0% mol from theory. The output of 3-cyanopyridine was 89.2 $gl^{-1}h^{-1}$.

Example 3

A catalyst was prepared from 36.4 g of vanadiumpentoxide, 64.0 g of titanium dioxide, 98.6 g of zirconium dioxide and 0.2 g of $MoO_3$ in the molar ratio $V_2O_5$:$TiO_2$:$ZrO_2$=1:4:4 and 0.54% wt. % $MoO_3$ based on $V_2O_5$.

The catalyst was prepared by the method described in the example 1. The gaseous feed consisting of 2-methyl-5-ethylpyridine air, ammonia and water vapour was passed through the catalyst bed (60 cm$^3$) at a temperature of 320° C. The feeding rate (gram per 1 liter catalyst per 1 hour=$gl^{-1}h^{-1}$) was: 2-methyl-5-ethylpyridine—72 $gl^{-1}h^{-1}$, air—1500 liters, ammonia—228 $gl^{-1}h^{-1}$, water 700 $gl^{-1}h^{-1}$ corresponding to a molar ratio of 2-methyl-5-ethylpyridine:$O_2$:$NH_3$:$H_2O$ of 1:47:45:130. Accordingly 21.6 g of 2-methyl-5-ethylpyridine was fed over 10 hours. The conversion was complete. 15.3 g 3-cyanopyridine was obtained corresponding to a yield of 82.2% based on the feed of 2-methyl-5-ethylpyridine. The output of 3-cyanopyridine was 50.8 $gl^{-1}h^{-1}$.

Example 4

A catalyst with a molar ratio of $V_2O_5$:$TiO_2$:$ZrO_2$=1:4:4 and 0.90 wt. % of $MoO_3$ based on $V_2O_5$ was prepared according to example 1. A mixture consisting of 3-methylpyridine, air, ammonia was passed through the catalyst at a temperature of 330° C. The feeding rate (gram per 1 liter catalyst per 1 hour=$gl^{-1}h^{-1}$) was: 3-methylpyridine—84 $gl^{-1}h^{-1}$, air—2000 liters, ammonia—9.92 $gl^{-1}h^{-1}$ corresponding to a molar ratio of 3-methylpyridine:$O_2$:$NH_3$ of 1:40:1.3. Accordingly 25.2 g of 3-methylpyridine was fed over 10 hours. The conversion was complete. 27.3 g 3-cyanopyridine was obtained corresponding to a yield of 97.9% from theory. The output of 3-cyanopyridine was 91.0 $gl^{-1}h^{-1}$.

Example 5

A catalyst with a molar ratio of $V_2O_5$:$TiO_2$:$ZrO_2$=1:4:8 and 0.98 wt. % of $MoO_3$ based on $V_2O_5$ was prepared according to example 1. A mixture consisting of 2-methyl-5-ethylpyridine, air, ammonia and water vapour was passed through the catalyst at a temperature of 320° C. The feeding rate (gram per 1 liter catalyst per 1 hour=$gl^{-1}h^{-1}$) was: 2-methyl-5-ethylpyridine—72 $gl^{-1}h^{-1}$, air—1500 liters, ammonia—228 $gl^{-1}h^{-1}$ and water—700 $gl^{-1}h^{-1}$ corresponding to a molar ratio of 2-methyl-5-ethylpyridine:$O_2$:$NH_3$:$H_2O$ of 1:47:45:130. Accordingly 21.6 g of 2-methyl-5-ethylpyridine was fed over 10 hours. The conversion was complete. 15.4 g of 3-cyanopyridine was obtained corresponding to a yield of 83% based on the feed of 2-methyl-5-ethylpyridine. The output of 3-cyanopyridine was 513 $gl^{-1}h^{-1}$.

Example 6

A catalyst with a molar ratio $V_2O_5$:$TiO_2$:$ZrO_2$=1:4:8 and 1.15 wt % of $MoO_3$ based on $V_2O_5$ was prepared according to example 1. A mixture consisting of 3-methylpyridine, air, ammonia was passed through the catalyst at a temperature of 325° C. The feeding rate (gram per 1 liter catalyst per 1 hour=$gl^{-1}h^{-1}$) was: 3-methylpyridine—168 $gl^{-1}h^{-1}$, air—2000 liters, ammonia—22.8 $gl^{-1}h^{-1}$ corresponding to a ratio of 3-methylpyridine:$O_2$:$NH_3$ of 1:40:1.5. Accordingly 50.4 g of 3-methylpyridine was fed over 10 hours. The conversion was complete. 55.8 g of 3-cyanopyridine was obtained corresponding to a yield of 99.0% from theory. The output of 3-cyanopyridine was 186 $gl^{-1}h^{-1}$.

Example 7

A catalyst with the molar ratio $V_2O_5$:$TiO_2$:$ZrO_2$=1:4:8 and 1.15 wt % of $MoO_3$ based on $V_2O_5$ was prepared according to example 1. A mixture consisting of 3-methylpyridine, air, ammonia was passed through the catalyst at a temperature of 350° C. The feeding rate (gram per 1 liter catalyst per 1 hour=$gl^{-1}h^{-1}$) was 3-methylpyridine—218 $gl^{-1}h^{-1}$, air—2000 liters, ammonia—30.35 $gl^{-1}h^{-1}$ corresponding to a molar ratio of 3-methylpyridine:$O_2$:$NH_3$ of 1:16:1.5. Accordingly 65.5 g of 3-methylpyridine was fed over 10 hours. The conversion was complete. 75.2 g of 3-cyanopyridine was obtained corresponding to a yield of 99.0% from theory. The output of 3-cyanopyridine was 241.7 $gl^{-1}h^{-1}$.

Example 8

1.167 kg of vanadiumpentoxide, 2.512 kg of titaniumdioxide as metatitanic acid, 6.322 kg of zirconiumdioxide and 12.4 g of ammoniumparamolybdate (molybdic acid) in the molar ratio $V_2O_5$:$TiO_2$:$ZrO_2$=1:4:8 and 1.05% $(NH_4)_6Mo_7O_{24} \cdot 4H_2O$ based on vanadiumpentoxide, were kneaded in a double-arm kneader and ground and mixed in a ball mill. The mixture was formed into granules of approximately 3×3 mm and thermally treated at a temperature of 100°–120° C. for 6 hours. A quantity of the obtained catalyst (1 liter, 1.50 kg) was loaded into a tube reactor made of stainless steel (internal diameter 21 mm, length 3 meters). A mixture of reagents, consisting of 3-methylpyridine, air, nitrogen and ammonia, was passed through the catalyst at a temperature of 340° C. The feeding rate (gram per 1 liter catalyst per hour=$gl^{-1}h^{-1}$) was: 3-methylpyridine 80 $gl^{-1}h^{-1}$, air 200 liter.h$^{-1}$, nitrogen 1200 liter.h$^{-1}$, ammonia 37.5 $gl^{-1}h^{-1}$ corresponding to a molar ratio of 3-methylpyridine to ammonia to oxygen of 1:2.6:2.2. Accordingly 1920 g 3-methylpyridine was fed over 24 hours. The conversion was 99%. 1910 g of 3-cyanopyridine were obtained corresponding to a yield of 89%. The output of 3-cyanopyridine was 79.6 $gl^{-1}h^{-1}$

Example 9

A quantity of the obtained catalyst from example 8 (985 cm$^3$, 1.46 kg) was loaded into a tube reactor made of stainless steel (internal diameter 21 mm, length 3 meters). A mixture of reagents, consisting of 3-methylpyridine, air, recycled exhaust gas and ammonia, was passed through the catalyst at a temperature of 345° C. The feeding rate (gram per 1 liter catalyst per hour=$gl^{-1}h^{-1}$) was: 3-methylpyridine 80 g$l^{-1}h^{-1}$, air 180 liter.h$^{-1}$, recycled exhaust gas 1200 liter.h$^{-1}$, ammonia 52.5 g$l^{-1}h^{-1}$ corresponding to a molar ratio of 3-methylpyridine to ammonia to oxygen of 1:3.6:2.0. Accordingly 1890 g 3-methylpyridine was fed over 24 hours. The conversion was 98.5%. 1850 g of 3-cyanopyridine were obtained corresponding to a yield of 88.5%. The output of 3-cyanopyridine was 77 g$l^{-1}h^{-1}$.

Example 10

A quantity of the obtained catalyst from example 8 (135 cm$^3$, 160 g) was thermally treated at 620° C. for 6 hours. This was loaded into a tube reactor made of stainless steel (internal diameter 21 mm, length 1000 mm). A mixture of reagents, consisting of 3-methylpyridine, air, nitrogen and ammonia, was passed through the catalyst at a temperature of 375° C. The feeding rate was: 3-methylpyridine 11 gh$^{-1}$ (81 g$l^{-1}h^{-1}$=gram per 1 liter catalyst per hour), air 30 liter.h$^{-1}$, nitrogen 285 liter.h$^{-1}$, ammonia 4 gh$^{-1}$ corresponding to a molar ratio of 3-methylpyridine to ammonia to oxygen of 1:2:2.6. Accordingly 264 g 3-methylpyridine was fed over 24 hours. The conversion was 99%. 261 g of 3-cyanopyridine were obtained corresponding to a yield of 89%. The output of 3-cyanopyridine was 80 g$l^{-1}h^{-1}$.

molar ratio of V$_2$O$_5$ to TiO$_2$ to ZrO$_2$ of from 1:1:2 to 1:12:25 and having a MoO$_3$ content of 0.54 to 2.6 weight percent, relating to V$_2$O$_5$.

2. Catalytic composition as claimed in claim 1 having a molar ratio of V$_2$O$_5$ to TiO$_2$ to ZrO$_2$ of from 1:3:4 to 1:8:16 and having a MoO$_3$ content of 0.54 to 1.15 weight percent, relating to V$_2$O$_5$.

3. Process comprising using the catalytic composition of claim 1 for the oxidative ammonolysis of an alkylpyridine.

4. Process according to claim 3 wherein said catalytic composition is used for the oxidative ammonolysis of 3-methylpyridine or 2-methyl-5-ethylpyridine.

5. Process for the preparation of a cyanopyridine by oxidative ammonolysis of an alkylpyridine, comprising passing the alkylpyridine together with ammonia, an oxygen-containing gas and, if necessary, water vapor over the catalytic composition as claimed in claim 1 at a temperature of from 280° C. to 400° C.

6. Process according to claim 5 for the preparation of 3-cyanopyridine by oxidative ammonolysis of 3-methylpyridine, comprising passing the 3-methylpyridine, ammonia and an oxygen-containing gas, calculated to O$_2$, in a molar ratio of from 1:1:1.5 to 1:8.5:60 over said catalytic composition at a temperature of from 310° C. to 380° C.

TABLE I

Oxidative ammonolysis of 2-methyl-5-ethylpyridine (MEP)

| | ratio of the catalyst components | | | | | | | | | | 3-cyanopyridine | |
|---|---|---|---|---|---|---|---|---|---|---|---|---|
| | in mol | | | in wt. % relating to V$_2$O$_5$ | feed g/l of cat. per hour | | | | Temperature, °C. | Conversion, % | molar yield, % | output g/l of cat./h |
| example | V$_2$O$_5$ | TiO$_2$ | ZrO$_2$ | MoO$_3$ | MEP | air | ammonia | water | | | | |
| 11 | 1 | 4 | 10 | 1.15 | 72 | 1500 | 228 | 583.3 | 320 | 100 | 80.7 | 50.0 |
| 12 | 1 | 4 | 12 | 0.54 | 72 | 1500 | 228 | 700 | 320 | 100 | 79.0 | 48.9 |
| 13 | 1 | 5 | 16 | 0.90 | 76 | 1500 | 228 | 700 | 320 | 100 | 78.5 | 51.7 |
| 14 | 1 | 3 | 8 | 0.90 | 126.6 | 1500 | 228 | 1000 | 340 | 100 | 78.5 | 85.2 |
| 15 | 1 | 4 | 8 | 0.90 | 134.7 | 1500 | 228 | 1000 | 360 | 100 | 78.0 | 90.0 |
| 16 | 1 | 1 | 6 | 1.15 | 72 | 1500 | 228 | 700 | 320 | 100 | 62.0 | 42.5 |
| 17 | 1 | 4 | 18 | 0.90 | 72 | 1500 | 228 | 700 | 320 | 100 | 74.0 | 50.8 |
| 18 | 1 | 6 | 2 | 0.54 | 72 | 1500 | 228 | 700 | 340 | 100 | 67.0 | 46.0 |

Table II

Oxidative ammonolysis of 3-methylpyridine (3-Pic)

| | ratio of the catalyst components | | | | | | | | | 3-cyanopyridine | |
|---|---|---|---|---|---|---|---|---|---|---|---|
| | in mol | | | in wt. % relating to V$_2$O$_5$ | feed g/l of cat. per hour | | | Temperature, °C. | Conversion, % | molar yield, % | output g/l of cat./h |
| example | V$_2$O$_5$ | TiO$_2$ | ZrO$_2$ | MoO$_3$ | 3-Pic | air | ammonia | | | | |
| 19 | 1 | 10 | 8 | 0.90 | 84 | 2000 | 11.4 | 325 | 100 | 82.0 | 77.0 |
| 20 | 1 | 6 | 2 | 0.54 | 84 | 2000 | 11.4 | 330 | 100 | 90.0 | 84.6 |
| 21 | 1 | 4 | 10 | 1.15 | 84 | 2000 | 11.4 | 330 | 100 | 94.0 | 88.4 |
| 22 | 1 | 4 | 12 | 0.54 | 84 | 2000 | 11.4 | 325 | 100 | 95.0 | 89.3 |
| 23 | 1 | 5 | 16 | 0.90 | 84 | 2000 | 11.4 | 330 | 100 | 92.5 | 86.6 |
| 24 | 1 | 4 | 8 | 0.90 | 126 | 2000 | 17.1 | 330 | 100 | 99.2 | 139.9 |
| 25 | 1 | 4 | 8 | 0.90 | 136 | 2000 | 19.7 | 3501 | 100 | 99.0 | 151.3 |

We claim:

1. Catalytic composition consisting of the oxides of vanadium, titanium, zirconium and molybdenum having a 7. Process according to claim 6 wherein the molar ratio of 3-methylpyridine to ammonia to oxygen-containing gas is 1:1:2 to 1:4:60.

8. Process according to claim 5 for the preparation of 3-cyanopyridine by oxidative ammonolysis of 2-methyl-5-ethylpyridine, wherein the 2-methyl-5-ethylpyridine, ammonia, an oxygen-containing gas, calculated to $O_2$, and water vapor in a molar ratio of from 1:20:20:60 to 1:60:70:330 is passed over said catalytic composition at a temperature of from 310° C. to 380° C.

9. Process comprising using the catalytic composition of claim 2 for the oxidative ammonolysis of an alkylpyridine.

10. Process according to claim 9 wherein said catalytic composition is used for the oxidative ammonolysis of 3-methylpyridine or 2-methyl-5-ethylpyridine.

11. Process for the preparation of a cyanopyridine by oxidative ammonolysis of an alkylpyridine comprising passing the alkylpyridine together with ammonia, an oxygen-containing gas and, if necessary, water vapor over the catalytic composition as claimed in claim 2 at a temperature of from 280° C. to 400° C.

12. Process according to claim 11 for the preparation of 3-cyanopyridine by oxidative ammonolysis of 3-methylpyridine, comprising passing the 3-methylpyridine, ammonia and an oxygen-containing gas, calculated to $O_2$, in a molar ratio of from 1:1:1.5 to 1:8.5:60 over said catalytic composition at a temperature of from 310° C. to 380° C.

13. Process according to claim 12 wherein the molar ratio of 3-methylpyridine to ammonia to oxygen-containing gas is 1:1:2 to 1:4:60.

14. Process according to claim 11 for the preparation of 3-cyanopyridine by oxidative ammonolysis of 2-methyl-5-ethylpyridine, wherein the 2-methyl-5-ethylpyridine, ammonia, an oxygen-containing gas, calculated to $O_2$, and water vapor in a molar ratio of from 1:20:20:60 to 1:60:70:330 is passed over said catalytic composition at a temperature of from 310° C. to 380° C.

* * * * *